(12) United States Patent
Haas

(10) Patent No.: US 11,577,020 B1
(45) Date of Patent: Feb. 14, 2023

(54) PROTECTIVE CASE FOR INSULIN INFUSION SET

(71) Applicant: Caden Haas, Villa Rica, GA (US)

(72) Inventor: Caden Haas, Villa Rica, GA (US)

( * ) Notice: Subject to any disclaimer, the term of this patent is extended or adjusted under 35 U.S.C. 154(b) by 0 days.

(21) Appl. No.: 17/500,919

(22) Filed: Oct. 13, 2021

(51) Int. Cl.
*A61M 5/00* (2006.01)

(52) U.S. Cl.
CPC ............ *A61M 5/003* (2013.01); *A61M 5/002* (2013.01)

(58) Field of Classification Search
CPC .............................. A61M 5/003; A61M 5/002
USPC ................................ 206/571; 220/4.22, 4.23
See application file for complete search history.

(56) References Cited

U.S. PATENT DOCUMENTS

| | | | |
|---|---|---|---|
| 3,074,541 A | 1/1963 | Roehr | |
| 3,380,608 A * | 4/1968 | Morbeck | B29C 66/54 220/4.23 |
| 4,423,811 A * | 1/1984 | Knapp | B65D 43/162 220/4.23 |
| 4,524,868 A | 6/1985 | Buckley et al. | |
| 4,526,820 A * | 7/1985 | Haas | B60R 13/005 220/4.23 |
| 4,541,528 A * | 9/1985 | Holmes | G07D 9/004 220/4.23 |
| 4,681,567 A | 7/1987 | Masters et al. | |
| 4,838,871 A | 6/1989 | Luther | |
| 4,877,132 A | 10/1989 | Makris et al. | |
| 4,890,731 A * | 1/1990 | Mroz | A63B 60/00 206/579 |
| 5,011,475 A | 4/1991 | Olson | |
| 5,078,267 A | 1/1992 | Wright | |
| 5,090,564 A * | 2/1992 | Chimienti | A61M 5/3205 220/4.23 |
| 5,158,209 A * | 10/1992 | Reil | B65D 1/30 220/4.23 |
| 5,960,956 A | 10/1999 | Langanki et al. | |

(Continued)

FOREIGN PATENT DOCUMENTS

| | | |
|---|---|---|
| CA | 2869624 | 10/2013 |
| WO | 2003068305 | 8/2003 |

OTHER PUBLICATIONS

"New Cosmetic Compact Empty Makeup Case Plastic Private Label Eye Shadow Palette Round Single Eyeshadow Packaging", https://www.alibaba.com/product-detail/New-cosmetic-compact-empty-makeup-case_1600200214902.html, published as of Aug. 13, 2021 or earlier.

(Continued)

*Primary Examiner* — Jacob K Ackun
(74) *Attorney, Agent, or Firm* — Emerson, Thomson & Bennett, LLC; Peter R. Detorre

(57) ABSTRACT

The present disclosure relates to a protective case for an insulin infusion set that can be used by diabetics to store the needle or needle and hub of an insulin infusion set when removed from the body to participate in various activities throughout the day. The insulin infusion set includes a first half shell and a second half shell connected together by a hinge and a port on its front side which allows a cannula or tube to pass through into the interior of the case to store the needle or needle and hub inside the case when in a closed configuration. The main body portion of the protective case and the port of the protective case may be various sizes and shapes as disclosed herein. The protective case may also be attached to an insulin pump housing or case through various means as disclosed herein.

19 Claims, 11 Drawing Sheets

(56) References Cited

U.S. PATENT DOCUMENTS

| | | | |
|---|---|---|---|
| 6,439,276 B1* | 8/2002 | Wood | A61M 5/3205 |
| | | | 141/97 |
| 6,595,362 B2 | 7/2003 | Penney et al. | |
| 7,093,595 B2 | 8/2006 | Nesbitt | |
| 7,407,493 B2 | 8/2008 | Cane | |
| 7,434,684 B1* | 10/2008 | Mabra | F42B 39/007 |
| | | | 220/4.23 |
| 7,497,348 B2* | 3/2009 | Johnson | B01F 35/421 |
| | | | 366/209 |
| 7,597,196 B2 | 10/2009 | Langone | |
| 7,717,897 B2 | 5/2010 | Burg et al. | |
| 8,544,645 B2 | 10/2013 | Edwards et al. | |
| 8,851,281 B2 | 10/2014 | Leabeater et al. | |
| D747,457 S | 1/2016 | Glace et al. | |
| D754,842 S | 4/2016 | Sonderegger et al. | |
| D754,843 S | 4/2016 | Sonderegger et al. | |
| D835,261 S | 12/2018 | Oakes | |
| 2007/0021729 A1 | 1/2007 | Mogensen et al. | |
| 2009/0200185 A1 | 8/2009 | Follman et al. | |
| 2010/0100050 A1 | 4/2010 | Cane | |
| 2013/0110046 A1* | 5/2013 | Nowak | A61M 5/002 |
| | | | 604/152 |
| 2013/0240393 A1 | 9/2013 | Bode et al. | |
| 2014/0074033 A1 | 3/2014 | Sonderegger et al. | |
| 2015/0174338 A1 | 6/2015 | Takemoto | |
| 2015/0203267 A1* | 7/2015 | Fellin | B65D 35/10 |
| | | | 222/105 |
| 2022/0189086 A1* | 6/2022 | Kamath | A61M 5/31525 |

OTHER PUBLICATIONS

"Old Original Antique Pocket Watch Open Stock Image—Image of Metal, Watch: 139716067", https://www.dreamstime.com/old-original-antique-pocket-watch-open-gentlemans-clear-numeral-face-second-hand-dial-image139716067, published as of Aug. 13, 2021.

Sephora Collection Colorful Eyeshadow Custom Palette Case: Review, Photos, https://thenotice.net/2013/02/sephora-collection-custom-palette-review, published at least as early as Aug. 13, 2021.

Lurrose Single Empty magnetic eyeshadow Case Empty Eyeshadow Palette Box Empty Magnetic Cosmetics Makeup Powder Sample Container 4Pcs 26mm, https://antigua.desertcart.com/products/175233855-lurrose-single-empty-magnetic-eyeshadow-case-empty-eyeshadow-palette-box-empty-magnetic-cosmetics-makeup-powder-sample, published at least as early as Aug. 13, 2021.

Yahoo Advertisement of Container for Dental Piece for Straightening Teeth, https://www.yahoo.com, published at least as early as Aug. 13, 2021.

* cited by examiner

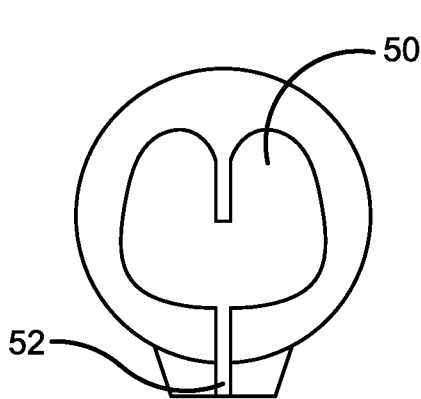 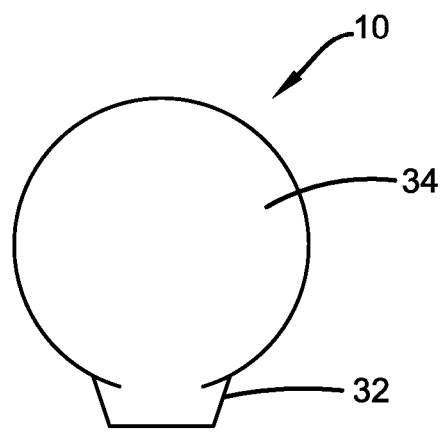
FIG. 5A  FIG. 5B
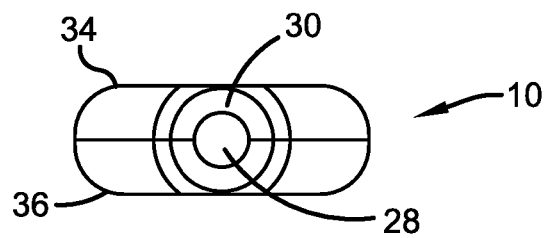
FIG. 5C
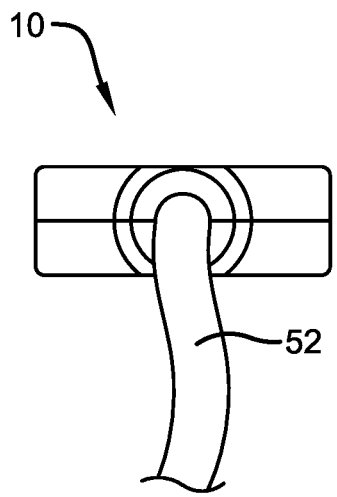 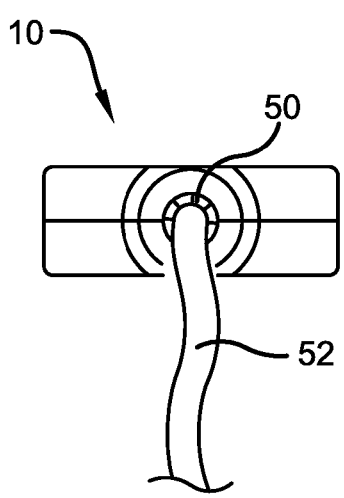 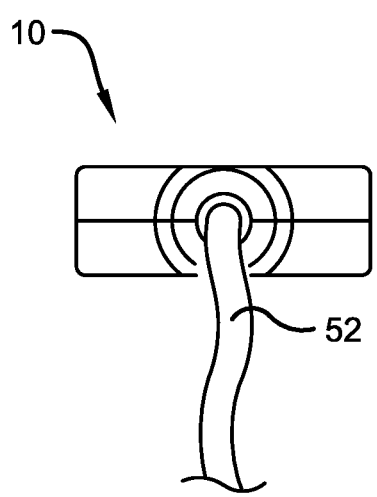
FIG. 6A  FIG. 6B  FIG. 6C

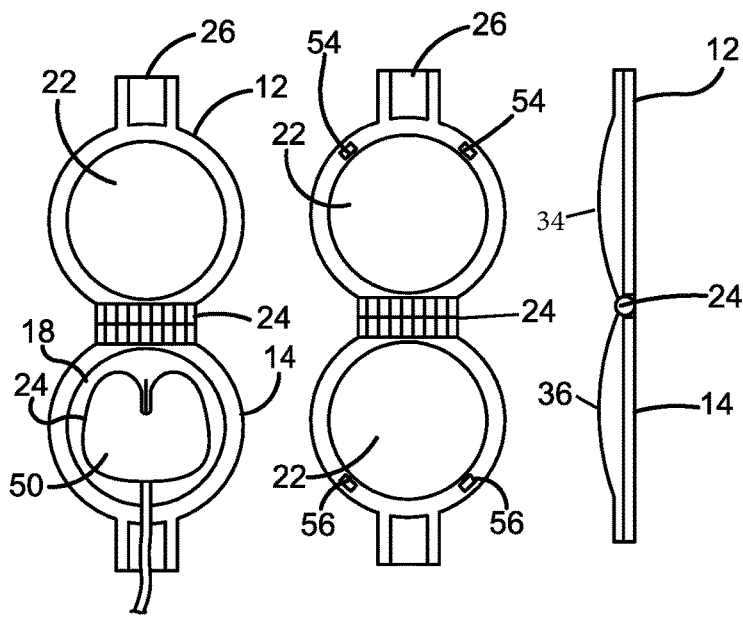
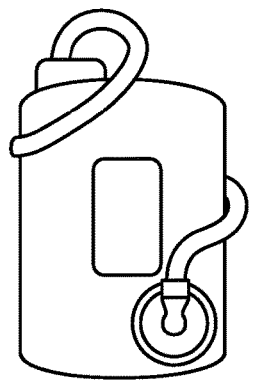
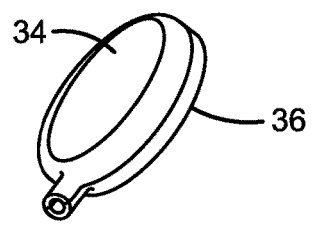
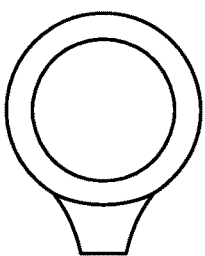
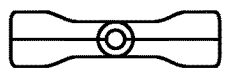
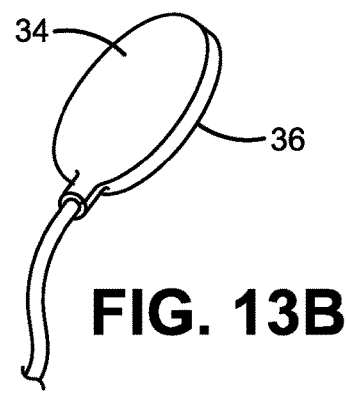
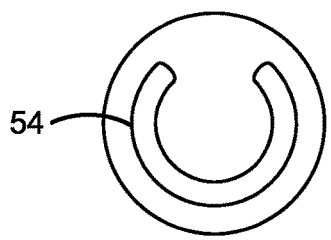
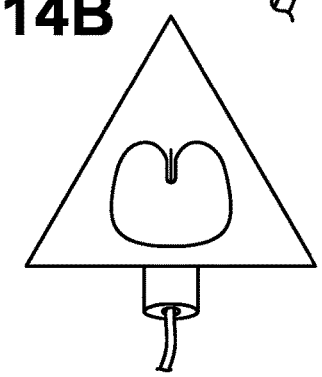
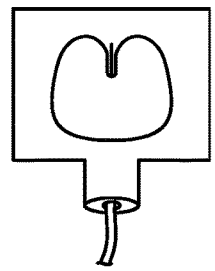
FIG. 7 FIG. 8 FIG. 9
FIG. 15
FIG. 13A
FIG. 10
FIG. 11
FIG. 12
FIG. 13B
FIG. 14B
FIG. 14A
FIG. 16 FIG. 17

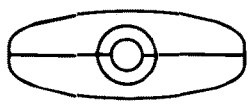  
FIG. 18A   FIG. 18B   FIG. 18C   FIG. 18D
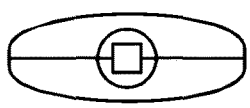  
FIG. 18E   FIG. 18F   FIG. 18G   FIG. 18H
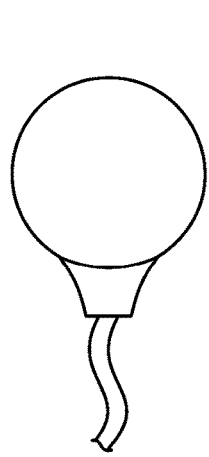 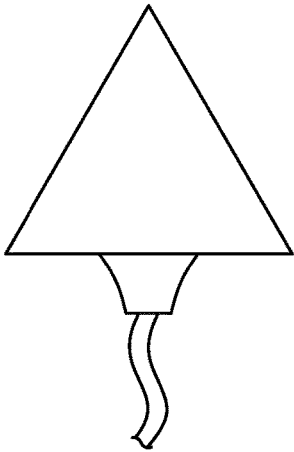 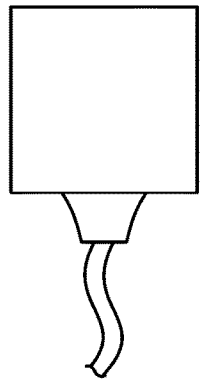 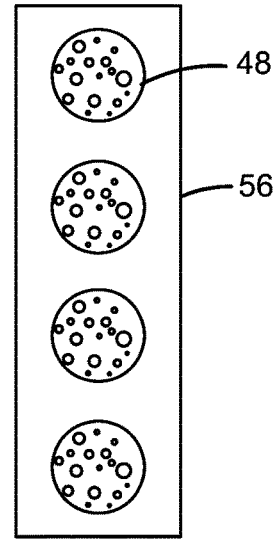
FIG. 19A   FIG. 19B   FIG. 19C
FIG. 20
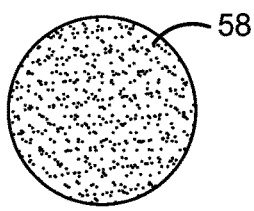 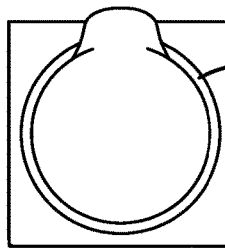 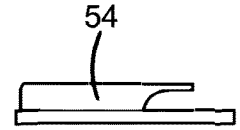 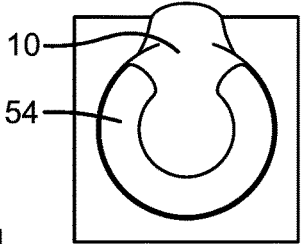
FIG. 21A   FIG. 22A   FIG. 22D   FIG. 22C
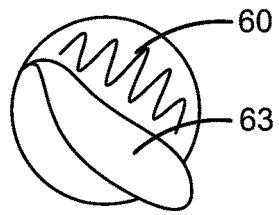 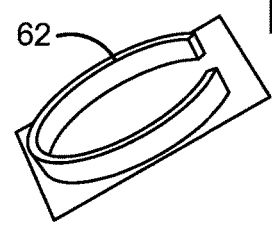 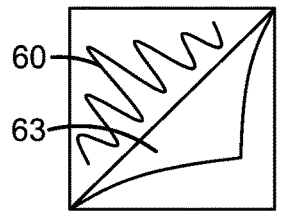
FIG. 21B   FIG. 22B   FIG. 22E

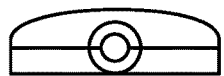   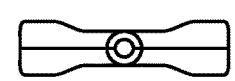
FIG. 23A  FIG. 23B  FIG. 23C  FIG. 23D
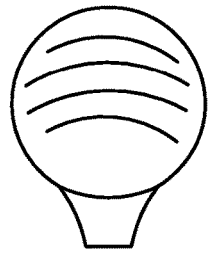 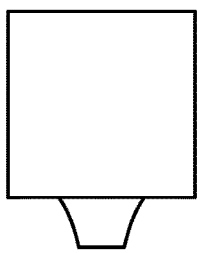 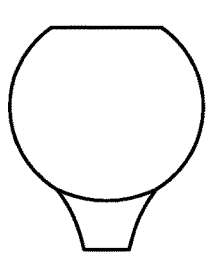 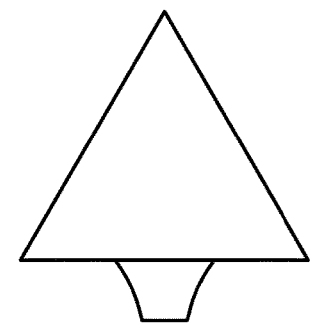
FIG. 24A  FIG. 24B  FIG. 24C  FIG. 24D
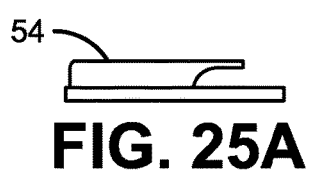  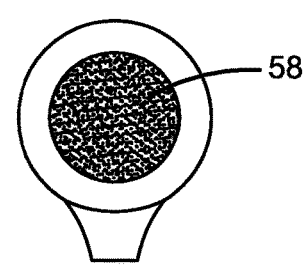
FIG. 25A  FIG. 26A
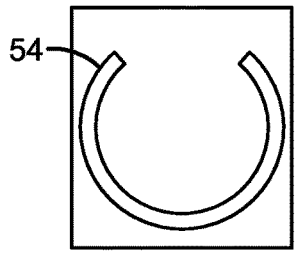 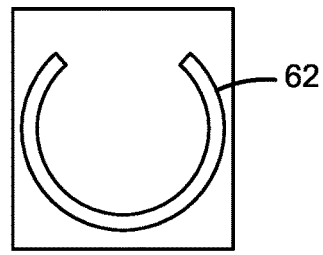
FIG. 27A
FIG. 25B  FIG. 26B
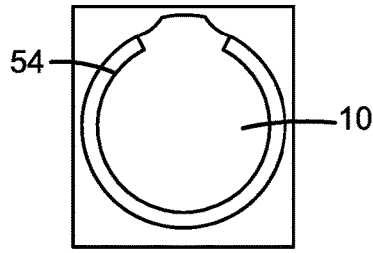 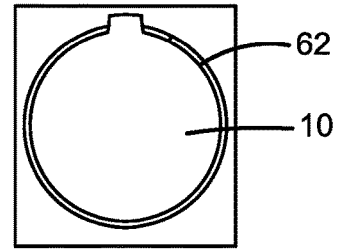 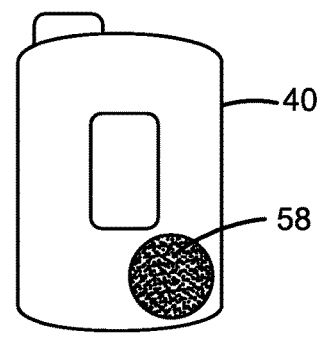
FIG. 25C  FIG. 26C  FIG. 27B

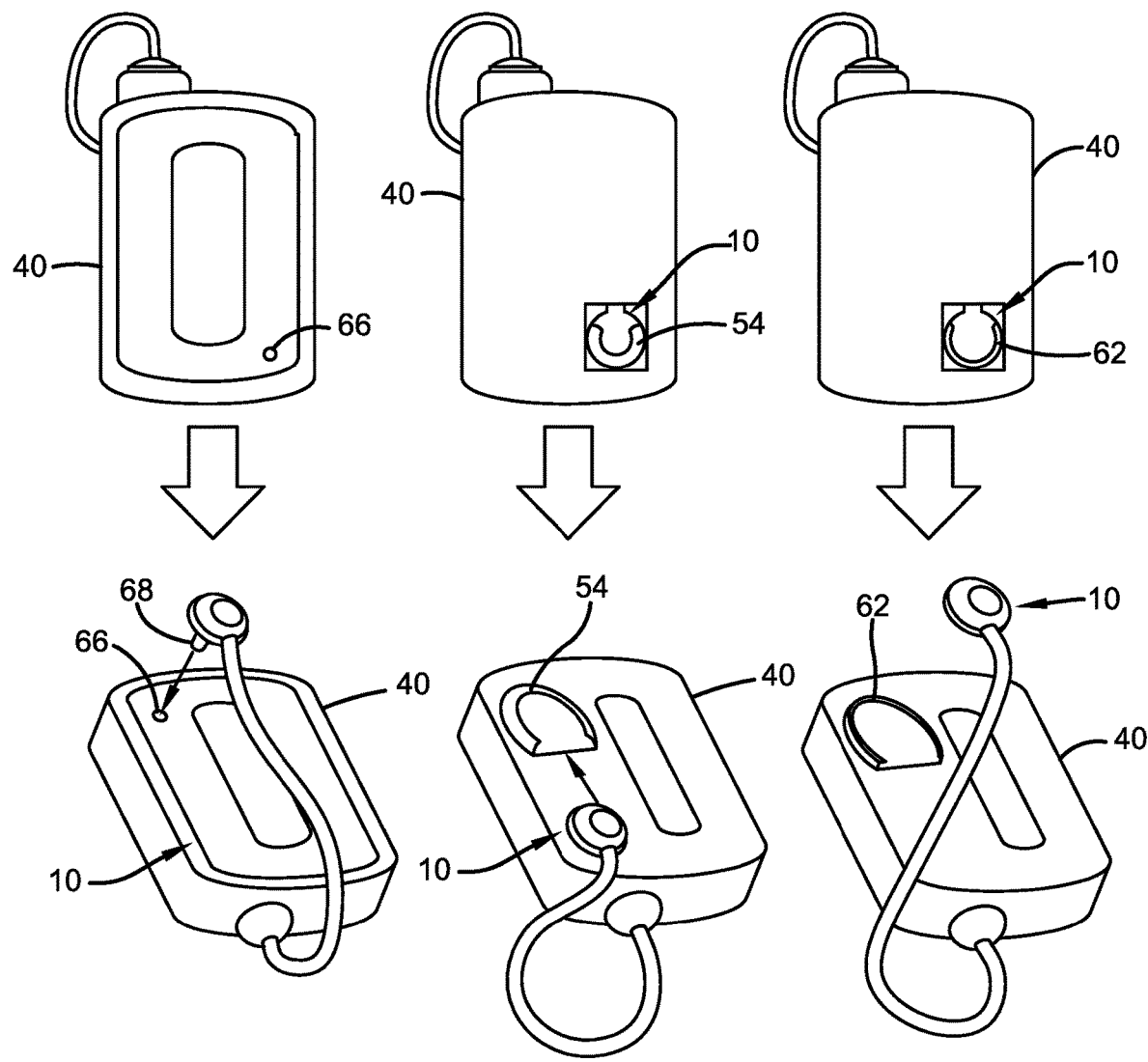
FIG. 44     FIG. 45     FIG. 46
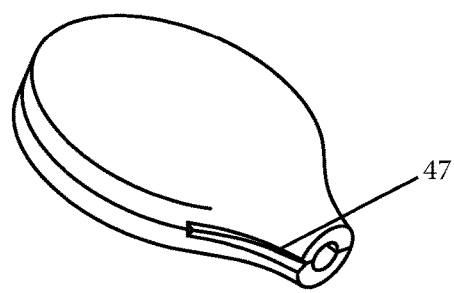
FIG. 47

PROTECTIVE CASE FOR INSULIN INFUSION SET

TECHNICAL FIELD

The present disclosure relates to a protective cover and a protective casing for an insulin infusion set. The protective cover and protective casing is designed to house a needle and a hub which are positioned at the end of an insulin infusion set.

BACKGROUND

Individuals with diabetes often elect to use insulin pumps. Insulin pumps provide a continuous flow of insulin 24 hours a day into the bodies and bloodstream of diabetics eliminating having to subject oneself to multiple daily injections. The continuous insulin injections provided by an insulin pump allow these individuals to better manage their blood sugar.

Insulin pumps provide an advantageous form for insulin injection for individuals who experience certain symptoms. For example, individuals who do not absorb food quickly and who have a severely negative reaction to low blood sugar may find an insulin pump beneficial for eliminating or at least reducing and relieving these negative symptoms. Other individuals may want to pause insulin flow while exercising or during certain activities which an insulin pump allows them to do. Other individuals who are planning to become pregnant may find an insulin pump to be a superior instrument for insulin delivery capable of preventing extreme and sudden drops in blood sugar.

Insulin pumps can be used by individuals with Type 1 or Type 2 diabetes but their use is more common with individuals with Type 1 diabetes. Insulin pumps provide several advantages including fewer insulin injections or needle poking and improved blood sugar levels resulting from a consistent flow of insulin into the body. They also provide the ability for individuals to adjust the amount of insulin delivered to the body during the day.

One advantage of insulin pumps is that they provide individuals with a greater degree of flexibility and privacy. Users may connect and disconnect the insulin pump from their bodies at will at any time during the day and may discretely conceal the insulin pump and its corresponding parts under their clothing in an inconspicuous manner so that it is not visible and does not draw attention. For example, insulin pumps may be placed inside one's pocket or clipped to the waist of one's pants.

The parts of an insulin pump include a computerized pump programmed to meet the patient's specific insulin requirements, a container for holding the insulin and an infusion set. The infusion set includes a thin plastic tubing which is used for delivering insulin from the pump to the patient. At the end of the tubing, the infusion set includes a cannula including a needle and hub or a stainless steel needle which is inserted into the body. At certain times of the day, the patient or user may desire to disconnect the needle and hub of the infusion set from the body. For example, an individual may desire to remove the infusion set prior to taking a shower, to go to the beach, to participate in various sports or outdoor activities (e.g., wrestling, football, soccer, swimming, etc.), to exercise, etc. When disconnected, the insulin infusion set is exposed to the environment causing it to become contaminated. The insulin infusion set is also a delicate piece of equipment which means it is prone to being damaged by unpredictable events which may crush, tear or otherwise destroy the functionality of the insulin infusion set including the needle and hub. What is needed, therefore, is a safe and sanitary place for a user to store the needle and hub of an insulin infusion set while it is disconnected from the user's body.

SUMMARY

Provided is a protective case for an insulin infusion set. The protective case includes the following features: a first half shell having a front side, a back side a top interior portion, a rim portion and a first exterior portion; a second half shell having a front side, a back side, a bottom interior portion, a rim portion and a second exterior portion; a hinge connecting the back side of the first half shell to the back side of the second half shell, wherein the hinge allows the first half shell and second half shell to rotate with respect to each other between an open configuration and a closed configuration; an interior portion formed by the first half shell and second half shell of the protective case; and a port, wherein the port is formed from a port passageway formed at the front side of the first half shell and the front side of the second half shell when the first half shell and the second half shell are in a closed configuration.

According to further aspects of the present teaching, the port passageway at the front side of the first half shell and the port passageway at the front side of the second half shell is hemi-circular, hemi-cylindrical, hemi-spherical, hemi-prismal, or hemi-conical in shape and extends toward the interior portion of the protective case when the protective case is in the open configuration and the port passageway at the front side of the first half shell and the front side of the second half shell is circular, cylindrical, spherical, prismal or conical in shape and extends toward the interior portion of the protective case when the protective case is in the closed configuration.

According to further aspects of the present teaching, the port passageway is formed from a hemi-circular or hemi-cylindrical indentation along the rim of the first half shell and the rim of the second half shell.

According to further aspects of the present teaching, the port passageway on the first half shell and the port passageway on the second half shell when in the closed configuration forms one of a conical shaped port, a spherical shaped port, a triangular shaped port, a square or cubical shaped port, a rectangular shaped port, a pentagonal shaped port, a hexagonal shaped port, a heptagonal shaped port, an octagonal shaped port, a nonagonal shaped port, a decagonal shaped port, or a star shaped port having from 5 to 10 points.

According to further aspects of the present teaching, the port passageway includes a seal along a periphery of its opening, wherein the seal is formed by a seal portion positioned along a periphery of the port passageway of the first half shell and along a periphery of the port passageway of the second half shell.

According to further aspects of the present teaching, the port passageway of the protective case is formed in a port portion of the protective case, wherein the port portion is formed from an outward symmetrical protection of a primary shape of the first half shell and the second half shell of the protective case, wherein the port portion includes the port passageway, when the first half shell and the second half shell are in the closed configuration.

According to further aspects of the present teaching, the bottom interior portion includes a sanitizer positioned therein, wherein the sanitizer is in the form of a fluid or a sanitizer pad, wherein the sanitizer pad is an alcohol pad.

According to further aspects of the present teaching, the top interior portion of the first half shell and/or the bottom interior portion of the second half shell includes a mold having a cut-out in the shape of a needle or a needle and hub of an insulin infusion set.

According to further aspects of the present teaching, the top interior portion of the first half shell and/or the bottom interior portion of the second half shell includes a polyurethane or polyethylene foam that a needle or a needle and hub of an insulin infusion set may rest upon.

According to further aspects of the present teaching, the top interior portion of the first half shell and the bottom interior portion of the second half shell each includes one of a sanitizer insert or pad, a mold cutout in the shape a needle or a needle and hub of an insulin infusion set or a polyurethane or polyethylene foam pad, wherein the polyurethane or polyethylene foam pad may optionally saturated in a sanitizer solution or wherein one of the top interior portion of the first half shell or the bottom interior portion of the second half shell includes one of a sanitizer insert or pad, a mold cutout in the shape a needle or a needle and hub of an insulin infusion set or a polyurethane or polyethylene foam pad, wherein the polyurethane or polyethylene foam pad may optionally saturated in a sanitizer solution and the other of the top interior portion of the first half shell or the bottom interior portion of the second half shell is empty.

According to further aspects of the present teaching, the rim portion of the first half shell extends at least a portion along the periphery of the top interior portion from a first side of the hinge to a second side of the hinge and wherein the rim portion of the second half shell extends at least a portion along the periphery of the bottom interior portion from the first side of the hinge to the second side of the hinge, wherein the rim portion of the first half shell has a different circumferential size than the rim portion of the second half shell allowing for a snap fit or pressure fit connection when the first half shell and the second half shell are in the closed configuration.

According to further aspects of the present teaching, the first half shell and the second half shell, excluding the port form a main body of the protective case, wherein the main body of the protective case may have a circular or polygonal shape.

According to further aspects of the present teaching, the first exterior portion of the first half shell and/or the second exterior portion of the second half shell is concave in shape, convex in shape, has an indented portion, has a flat or level planar shape or has a tapered side portion around its circumference.

According to further aspects of the present teaching, the protective case is made from a plastic material, a synthetic fabric, a natural fabric or a metal.

According to further aspects of the present teaching, the protective case includes a hardened material or a pliable material.

According to further aspects of the present teaching, the port includes a first side portion and a second side portion, wherein the first side portion and second side portion of the port comprises an angled cut-out portion in the closed configuration, wherein the angled cut-out portion is formed from a port portion of the first half shell having an angled portion on the first side portion and second side portion of the first half shell port portion and a port portion of the second half shell having an angled portion of the first side portion and the second side portion of the second half shell port portion.

According to further aspects of the present teaching, the protective case includes a push button latching mechanism positioned on the front side of the protective case.

According to further aspects of the present teaching, includes an insulin pump attachment mechanism, wherein the insulin pump attachment mechanism comprises one of the following: i) a hook and loop fastener, wherein a first fastener comprising a hook or loop is attached to either the first exterior portion of the first half shell or the second exterior portion of the second half shell and a corresponding second fastener, comprising a hook if the first fastener is a loop or loop if the first fastener is a hook, is attached to a housing of an insulin pump, ii) a protective case snap connector fitted onto the housing of an insulin pump for connecting the protective case to the housing of the insulin pump, iii) a button connector comprising a post end and a receiving end wherein one of the post end and the receiving end is positioned on one of the first exterior surface of the first half shell or the second exterior surface of the second half shell and wherein the opposing post end or receiving end is positioned on the housing of the insulin pump and iv) a sleeve positioned on the housing of the insulin pump for receiving the protective case, wherein the sleeve has a shape which corresponds to the shape of the protective case.

Also provided is a first kit. The first kit includes an insulin infusion set comprising a needle, a hub and a cannula; and a protective case for storing the needle and the hub of an insulin infusion set, wherein the protective case includes: a first half shell having a front side, a back side a top interior portion, a rim portion and a first exterior portion; a second half shell having a front side, a back side, a bottom interior portion, a rim portion and a second exterior portion; a hinge connecting the back side of the first half shell to the back side of the second half shell, wherein the hinge allows the first half shell and second half shell to rotate with respect to each other between an open configuration and a closed configuration; an interior portion formed by the first half shell and second half shell of the protective case; a port, wherein the port is formed from a port passageway formed at the front side of the first half shell and the front side of the second half shell when the first half shell and the second half shell are in a closed configuration.

Also provided is a second kit. The second kit includes an insulin infusion set including a needle, a hub and a cannula; a protective case for storing the needle and the hub of an insulin infusion set, wherein the protective case includes: a first half shell having a front side, a back side a top interior portion, a rim portion and a first exterior portion; a second half shell having a front side, a back side, a bottom interior portion, a rim portion and a second exterior portion; a hinge connecting the back side of the first half shell to the back side of the second half shell, wherein the hinge allows the first half shell and second half shell to rotate with respect to each other between an open configuration and a closed configuration; an interior portion formed by the first half shell and second half shell of the protective case; a port, wherein the port is formed from a port passageway formed at the front side of the first half shell and the front side of the second half shell when the first half shell and the second half shell are in a closed configuration; an insulin pump comprising a housing, and an insulin pump attachment mechanism which is used to engage the protective case to the housing of the insulin pump, wherein the insulin pump attachment mechanism comprises one of the following: i) a hook and loop fastener, wherein a first fastener comprising a hook or loop is attached to either the first exterior portion of the first half shell or the second exterior portion of the second half shell and a corresponding second fastener, comprising a hook if the first fastener is a loop or loop if the first fastener is a hook, is attached to the housing of the insulin pump, ii) a protective case snap connector fitted onto the housing of an insulin pump for connecting the protective case to the housing of the insulin pump, iii) a button connector comprising a post end and a receiving end wherein one of the post end and the receiving end is positioned on one of the first exterior surface of the first half shell or the second exterior surface of the second half shell and wherein the opposing post end or receiving end is positioned on the housing of the insulin pump and iv) a sleeve positioned on the housing of the insulin pump for receiving the protective case, wherein the sleeve has a shape which corresponds to the shape of the protective case.

BRIEF DESCRIPTION OF THE DRAWINGS

FIG. 5A is a top view of an interior portion of an exemplary protective case for an insulin infusion set holding an insulin infusion set.

FIG. 5B is top view of an exemplary protective case for an insulin infusion set.

FIG. 5C is a front side view of an exemplary protective case for an insulin infusion set.

FIG. 6A is a front side view of an exemplary protective case for an insulin infusion set showing a pressure fit around an insulin tube as it enters the case.

FIG. 6B is a front side view of an exemplary protective case for an insulin infusion set showing a seal around an insulin tube as it enters the case.

FIG. 6C is a front side view of an exemplary protective case for an insulin infusion set showing a loose fit or space around an insulin tube as it enters the case.

FIG. 7 is a top view of an interior portion of an exemplary protective case for an insulin infusion set showing a sanitizer pad and insulin infusion set positioned therein.

FIG. 8 is a top view of an interior portion of an exemplary protective case for an insulin infusion set showing a hollow interior and push latch mechanism.

FIG. 9 is side view of an exemplary protective case for an insulin infusion set in an open configuration.

FIG. 10 is a top view of an exemplary protective case for an insulin infusion set having a concave top surface.

FIG. 11 is a side view of an exemplary protective case for an insulin infusion set having a convex top surface.

FIG. 12 is a side view of an exemplary protective case for an insulin infusion set having a concave top surface.

FIG. 13A is a perspective view of an exemplary concave protective case for an insulin infusion set in a closed configuration.

FIG. 13B is a perspective view of an exemplary convex protective case for an insulin infusion set in a closed configuration with an insulin tube passing through a port in the case.

FIG. 14A is a top view of an exemplary sleeve or pocket capable of receiving an exemplary protective case for an insulin infusion set.

FIG. 14B is a side view of an exemplary sleeve or pocket capable of receiving an exemplary protective case for an insulin infusion set.

FIG. 15 is a front side view of an exemplary insulin pump, sleeve, and protective case for an insulin infusion set.

FIG. 16 is a top view of an interior portion of exemplary protective case for an insulin infusion set and an insulin infusion set positioned therein.

FIG. 17 is a top view of an interior portion of exemplary protective case for an insulin infusion set and an insulin infusion set positioned therein.

FIGS. 18A through 18H are front side views of various exemplary protective cases for an insulin infusion set.

FIGS. 19A through 19C are top views of various exemplary protective cases for an insulin infusion set.

FIG. 20 is a planar view of an exemplary strip of pads which may be peeled off and placed in a protective case for an insulin infusion set.

FIG. 21A is a top view of an exemplary hook and loop (Velcro) pad that may be attached to the outside surface of a protective case for an insulin infusion set or to an insulin pump.

FIG. 21B is a bottom view of an exemplary hook and loop (Velcro) pad including an adhesive that may be exposed by a peel-away strip for attaching the hook and loop (Velcro) pad to the outside surface of a protective case for an insulin infusion set or to an insulin pump.

FIG. 22A is a planar view of an exemplary snap connector for engaging a protective case for an insulin infusion set.

FIG. 22B is a perspective view of an exemplary snap connector for engaging a protective case for an insulin infusion set.

FIG. 22C is a planar top view of an exemplary sleeve for engaging a protective case for an insulin infusion set.

FIG. 22D is a side view of an exemplary sleeve for engaging a protective case for an insulin infusion set.

FIG. 22E is a planar bottom view of an exemplary sleeve showing a peel-away adhesive for engaging exemplary sleeve to an insulin pump.

FIGS. 23A through 23D are front side views of exemplary protective cases for an insulin infusion set.

FIGS. 24A through 24D are top views of exemplary protective cases for an insulin infusion set.

FIG. 25A is a side view of a sleeve for a protective case for an insulin infusion set.

FIGS. 25B and 25C are top planar views of a sleeve for a protective case for an insulin infusion set with FIG. 25B illustrating a sleeve without a case and FIG. 25C illustrating a sleeve holding a case.

FIG. 26A is a side view of a snap fitting for a protective case for an insulin infusion set.

FIGS. 26B and 26C are top planar views of a snap fitting for a protective case for an insulin infusion set with FIG. 26B illustrating a snap fitting without a case and FIG. 26C illustrating a snap fitting holding a case.

FIG. 27A is a top planar view of an exemplary protective case for an insulin infusion set having an exemplary hook and loop (Velcro) connector adhered thereto.

FIG. 27B is a side planar view of an insulin pump having an exemplary hook and loop (Velcro) connector adhered thereto.

FIG. 44 illustrates an exemplary insulin pump and protective case having a button connector for engaging the protective case to the insulin pump.

FIG. 45 is a diagram illustrating the insertion of a protective case for an insulin infusion set into a sleeve on an insulin pump.

FIG. 46 is a diagram illustrating the engagement of a protective case for an insulin infusion set into a snap connector on an insulin pump.

FIG. 47 is a perspective view of an exemplary protective case for an insulin infusion set.

DETAILED DESCRIPTION

The present disclosure, as demonstrated by the exemplary embodiments disclosed herein, provides a device for storing a needle or needle and hub of an insulin infusion set (50). The device may be described as a case, casing, container or a protective case or container and is hereinafter referred to as a protective case. The protective case of the insulin infusion set may be any shape appropriate for its use as deemed suitable by a person of ordinary skill in the art. For example, the shape of the protective case may be circular, square, triangular or any other appropriate shape. The protective case may also be flat, convex (e.g., having a dome-like shape), or concave (e.g., have an indented shape) depending on the particular application and the type and size of the needle or needle and hub of the insulin infusion set (50). The protective case may also have a slim sleek design corresponding to the contour or profile of the insulin infusion set. Examples of various shaped protective cases are illustrated in FIGS. 18A through 18D. The protective case may also be any color that is aesthetically pleasing to the user including but not limited to red, blue, white, black etc. and may in certain cases include various color combinations including red/blue, black/white, green/yellow, etc. The protective case, including its various component parts may be made from any material as deemed by a person of ordinary skill in the art including but not limited to plastic, metal or 3-dimensional printing material.

Figure 30:
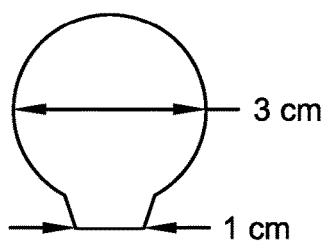
FIG. 30 is a diagram illustrating the dimensions of an exemplary protective case for an insulin infusion set.
Figure 31:
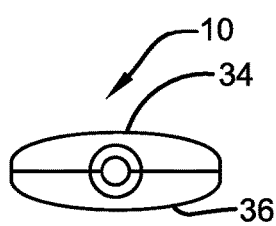
FIG. 31 is a front side view of an exemplary protective case for an insulin infusion set.
Figure 32:
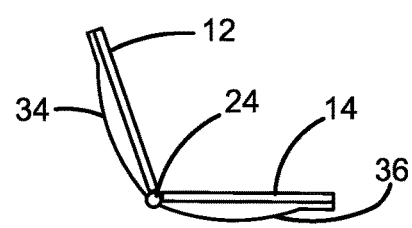
FIG. 32 is a side view of an exemplary protective case for an insulin infusion set in an open configuration.
Figure 33:
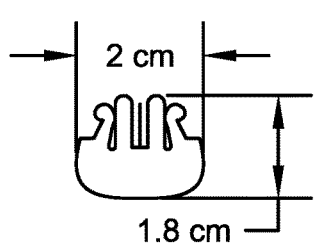
FIG. 33 is a diagram illustrating the dimensions of an exemplary insulin infusion set.
Figure 34:
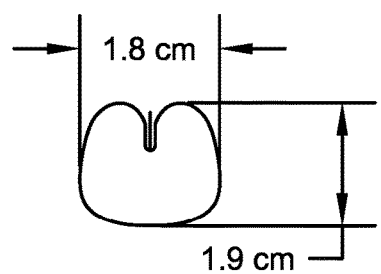
FIG. 34 is a diagram illustrating the dimensions of an exemplary insulin infusion set.
Figure 35A:
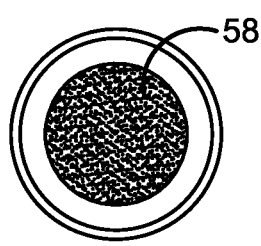
FIG. 35A is a top planar view of an exemplary protective case for an insulin infusion set having an exemplary hook and loop (Velcro) connector adhered thereto.
Figure 36A:
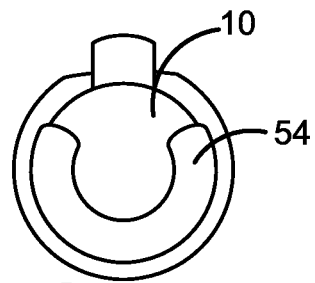
FIG. 36A is a top planar view of a protective case for an insulin infusion set inserted inside a sleeve.
Figure 35B:
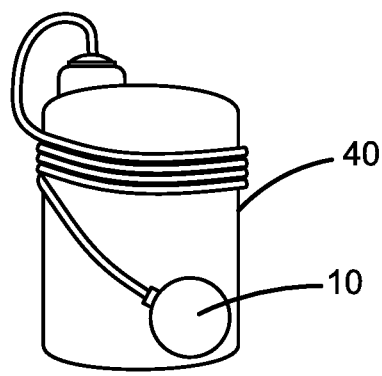
FIG. 35B illustrates an exemplary protective case for an insulin infusion set attached to an insulin pump through a hook and loop (Velcro) connector.
Figure 36B:
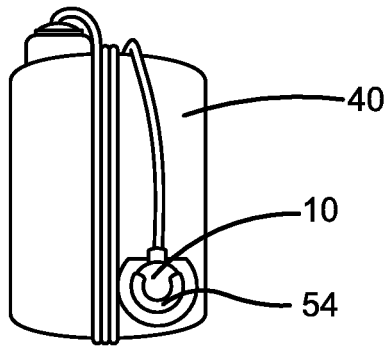
FIG. 36B illustrates an exemplary protective case for an insulin infusion set inserted inside a sleeve attached to an insulin pump.
Figure 35C:
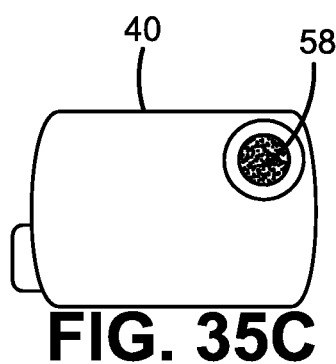
FIG. 35C illustrates an insulin pump having a hook and loop (Velcro) connector for engaging a protective case for an insulin infusion set.
Figure 36C:
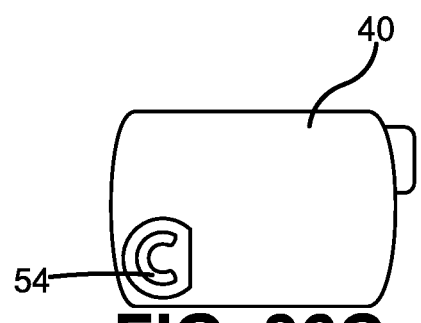
FIG. 36C illustrates an insulin pump having a sleeve attached thereto for receiving a protective case for an insulin infusion set.

It is noted that insulin infusion sets may vary in size and may have a length ranging from about 1.5 cm to about 2.5 cm, a width ranging from about 1.5 cm to about 2.5 cm and a height ranging from about 3 mm to about 10 mm (in some cases the height being about 7 mm). FIGS. 30, 33 and 34 show the length and width of typical insulin infusion sets. However, it is understood that the insulin infusion set may have any dimensional size as deemed suitable by the manufacturer.

Figure 28A:
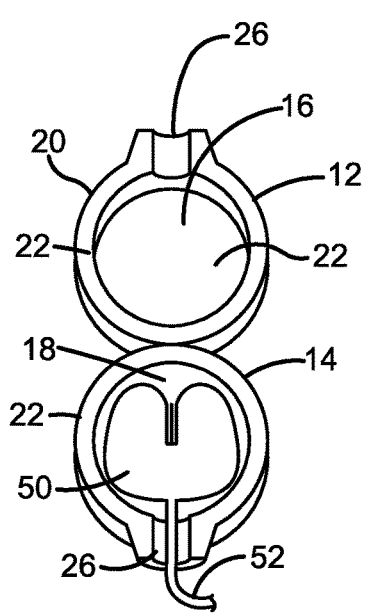
FIG. 28A is a top planar view of an interior portion of an exemplary protective case for an insulin infusion set containing an insulin infusion set.
Figure 28B:
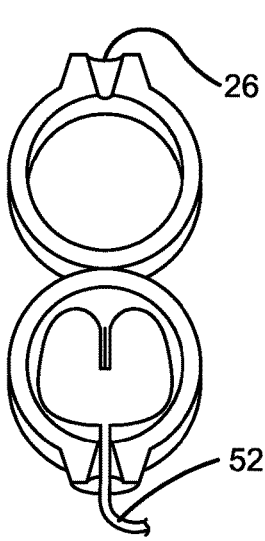
FIG. 28B is a top planar view of an interior portion of an exemplary protective case for an insulin infusion set containing an insulin infusion set.
Figure 29:
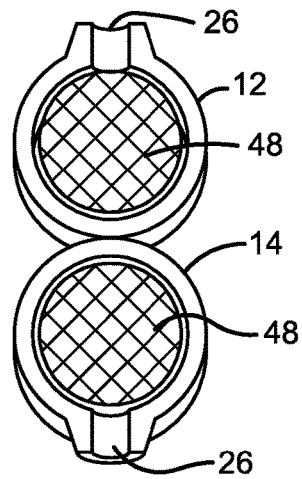
FIG. 29 is a top planar view of an interior portion of an exemplary protective case for an insulin infusion set containing a sanitizing pad.

FIGS. 1A, 1B, 1C and 1D illustrate a first exemplary protective case according to the present disclosure. The protective case (10) is circular in shape and has a first half shell (12) and a second half shell (14). The first half shell (12) and second half shell (14) may be described as having a top interior portion (16), a bottom interior portion (18), a rim portion (20), and an interior portion (22). The first half shell (12) and the second half shell (14) are joined together by a hinge (24) which allows the first half shell (12) and the second half shell (14) to be opened and closed. The protective case (10) also includes a port passageway (26) at its first half shell (12) and at its second half shell (14). The port passageway (26) may be hemi-circular or hemi-cylindrical in shape and extends towards an interior portion (22) of the protective case (10). When the first half shell (12) and the second half shell (14) are closed or in a closed configuration, half shaped port passageways (26), e.g., the hemi-circular or hemi-cylindrical port passageways (26) forms a port (28) or full shaped circular or cylindrical port (28). In certain cases, the port passageway (26) may be described as being formed from a hemi-circular or hemi-cylindrical indentation (see for example FIG. 28A) along top portion or rim of the first and second half shell (12), (14). However, it is also contemplated that the port passageway (26) may be any other shape (e.g., hemi-square-like, hemi-cubical, hemi-spherical hemi-conical (see for example FIG. 28B) or any other type of hemi-prism shape) deemed suitable by a person of ordinary skill in the art. Examples of shapes which may be used or formed in the indentation of the top portion or rim of the first and second half shell (10, 12) include but are not limited to a hemi-triangular shape or a hemi-triangular prism, a hemi-rectangular shape or a hemi-rectangular prism, a hemi-pentagonal or a hemi-pentagonal prism, a hemi-hexagonal shape or a hemi-hexagonal prism, a hemi-octagonal shape or a hemi-octagonal prism, etc. and when the first half shell (12) and the second half shell (14) are closed or in a closed configuration, the hemi-prism shaped or other hemi-shaped port forms a corresponding full shaped port (e.g., a triangular shaped port, a spherical port, a conical port which provides a contact point for securing a tube of an insulin infusion set (see FIG. 28B), a square or cubical port, a rectangular or rectangular shaped prism port, a pentagonal or pentagonal prism port, a hexagonal or hexagonal shaped prism port, an octagonal or octagonal shaped prism port, etc.). In another embodiment, the indentation at the top portion or rim of the first and second half shell (10, 12) may be a hemi-star shaped polygon or prism which when the first and second half shells (10, 12) are closed, form a star shaped polygon or star shaped prism opening allowing for the tube or cannula (52) of an insulin infusion set (50) to pass through. It is to be understood that the star shaped polygon or star shaped prism opening may include any number of points. In certain cases, the number of points of the star shaped polygon or star shaped prism may range from 5 to 10 or from about 5 to about 10. Examples of various shaped ports are illustrated in FIGS. 18A through 18H.

According to certain aspects of the present teaching, the port (28) may include a seal (30) positioned around the periphery of its opening. In certain embodiments, the seal (30) is formed by a seal portion positioned along the periphery of the port passageways (26) of the first and second half shells (12) and (14). Once the first and second half shells (12) and (14) are closed, the half seal portions of the two port passageways (26) join to form a single seal (30). This seal (30) maintains an opening present within the port (28) allowing for the tube or cannula of the insulin infusion set to be inserted therethrough. In certain embodiments, the seal is a silicone seal (50) as shown in FIG. 6B. The seal provides several advantages. First, it provides a means for securing the tube or cannula of the infusion set inside the protective case. This prevents movement of the needle or needle and hub of the insulin infusion set within the protective case (10) which may inadvertently cause damage to the needle or needle and hub of the insulin infusion set. Second, it provides a sterile environment within the interior of the protective case (10) as it prevents contaminants, debris, or other outside particles from entering inside the protective case (10) when the insulin infusion set is stored therein. This allows the insulin infusion set to remain clean and sterile prior to re-insertion into the user or patient's body as it is stored in a clean sterile environment. In the embodiment illustrated in FIG. 6B, the silicone seal (50) forms a wall around the tubing and functions as a water seal. FIG. 6A illustrates an alternative embodiment which does not include a seal but instead relies on pressure fitting the tube of an insulin infusion set into the port upon closing the protective case. FIG. 6C illustrates an alternative embodiment which does not include a seal in the port but instead relies on a loose fitting of the tube of an insulin infusion set into the port upon closing the protective case by providing a space between the exterior surface of the tube and the interior surface of the port.

Figure 42:
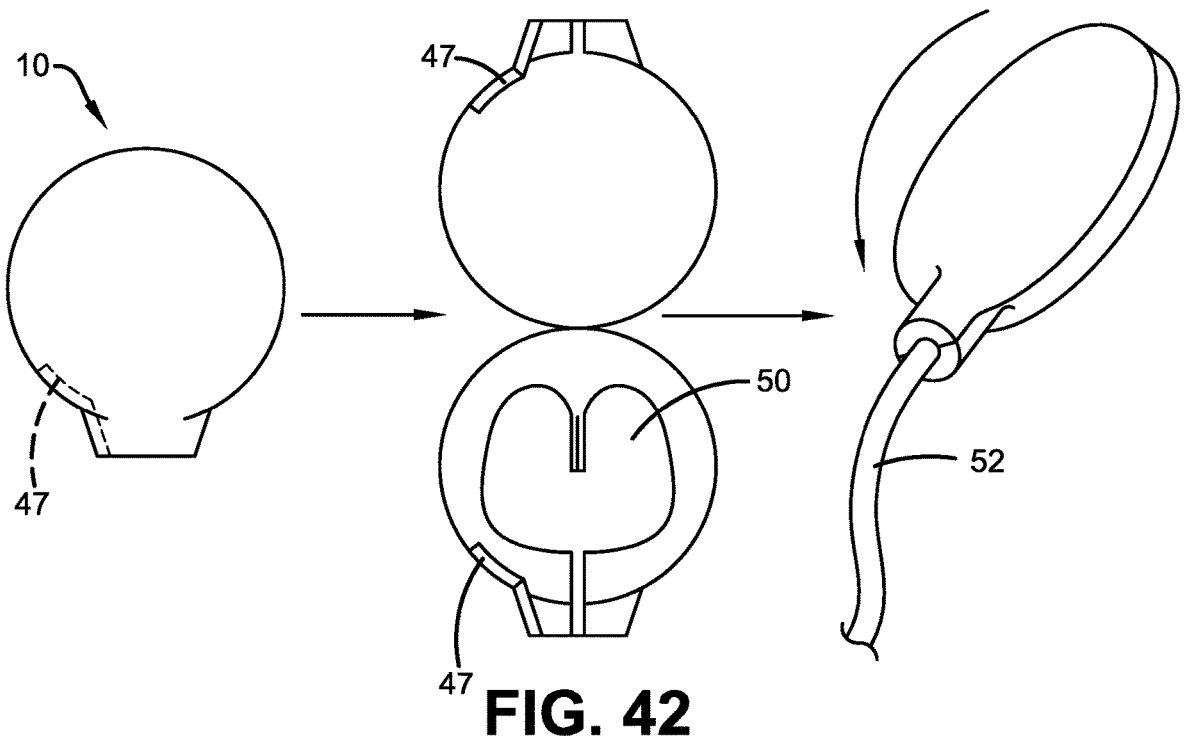
FIG. 42 is a diagram illustrating the opening and closing of a protective case for an insulin infusion set.
Figure 43:
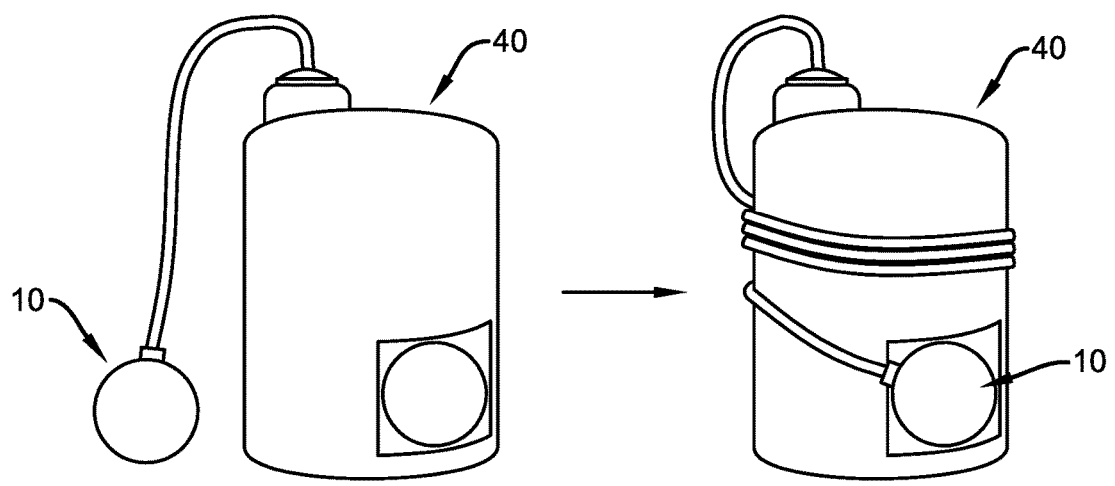
FIG. 43 is a diagram illustrating the attachment of a protective case for an insulin infusion set to an insulin pump.

According to certain aspects of the present teaching, the port (28) of the protective container (10) may be formed in a port portion (32) of the protective container (10). The port portion (32) of the protective container (10), may be formed from an outward symmetrical protrusion of a primary shape of the first and second half shells (12, 14) of the protective container (10). When in its closed configuration, the port portion of the protective container forms a passageway or (e.g., a cylindrical cavity) allowing for a tube or cannula of an insulin infusion set to pass through. The port portion (32) also providing a hardened shell around the passageway for the tube or cannula providing a means for protecting the tube or cannula from potential accidents and damage. According to further aspects of the present teaching, the port portion (32) may include a side indentation or cutout (47) formed by a cutout in one or both sides of the port portion of the first half shell (12) a cutout in one or both sides of the port portion of the second half shell (14) as shown in FIGS. 42 and 47. In other embodiments, the port portion (32) does not include a side indentation or cutout (42). In certain embodiments, the cutout (64) forms a V shape in the side of the port portion (32) when the protective case (10) is in its closed configuration. The indentation or cutout (64) is designed to allow users to insert their fingertips or a small edge tool into the space formed by the indentation or cutout to easily open the protective case (10). According to further aspects of the present teaching, the port portion (32) may have a greater degree of convexity than the remainder of the body of the protective case to accommodate the insertion point of the tube in the insulin infusion set. This may be achieved by port portions of the first half shell (12) and second half shell (14) curving outward to a greater degree than the main body of the protective container. An example of this feature is illustrated in FIG. 18C, however, this feature is contemplated as applicable to protective containers of any shape.

Figure 3:
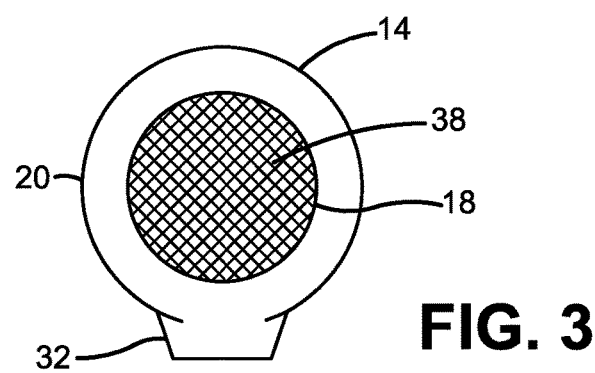
FIG. 3 is a top view of an interior portion of an exemplary protective case for an insulin infusion set.

In addition to the top interior portion (16) and the bottom interior portion (18), the first and second half shells (12) and (14) may also be described as respectively having a first exterior portion (34) and a second exterior portion (36). According to certain aspects of the present teaching, the bottom interior portion (18) may include a sanitizer (38) positioned therein as shown in FIG. 3. The sanitizer may be a fluid and in certain embodiments, the sanitizer may be applied to an insert or pad. For example, in certain embodiments, the sanitizer may be an alcohol pad (38), such as, for example, an isopropyl alcohol pad insert that rests inside the protective case (10) while storing the insulin infusion set. The sanitizer pad or insert may be changed out as needed to keep the insulin infusion set clean. Thus, the sanitizer assists in maintaining a clean and sterile interior environment for storing the needle or needle and hub of an insulin infusion set so that it may be reused and inserted into the user's or patient's body without being contaminated. In other arrangements, a sanitizer pad or wipe (e.g., an isopropyl pad or wipe) may also be used to clean the inside of the protective container (10) to maintain a sanitary environment for storing the insulin infusion set.

According to further aspects of the present teaching, the first or second exterior portions (34) of the protective container (10) may include a first side Velcro backing adhered thereto which may be used to engage a second side Velcro backing adhered to an insulin pump. Additional details concerning this aspect of the protective container (10) are described in greater detail below.

Figure 1A:
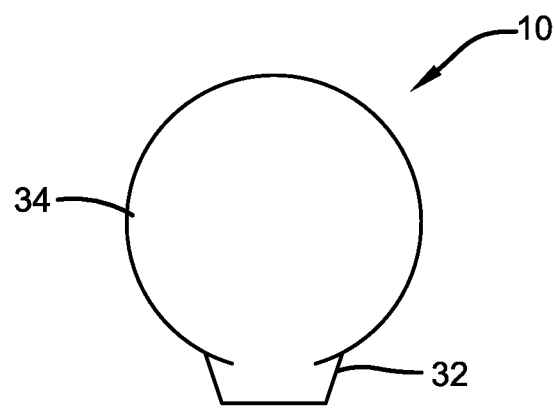
FIG. 1A is a top view of an exemplary protective case for an insulin infusion set.
Figure 1B:
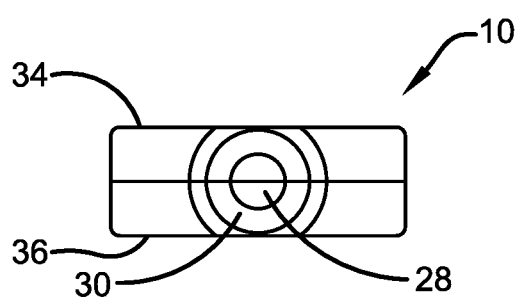
FIG. 1B is a front side view of an exemplary protective case for an insulin infusion set.
Figure 1D:
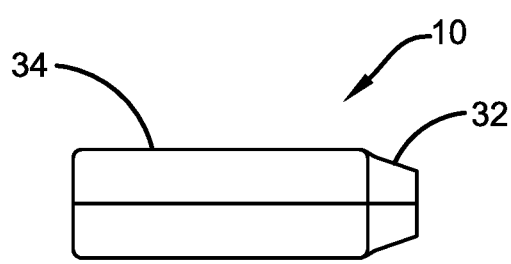
FIG. 1D is a side view of an exemplary protective case for an insulin infusion set.
Figure 1C:
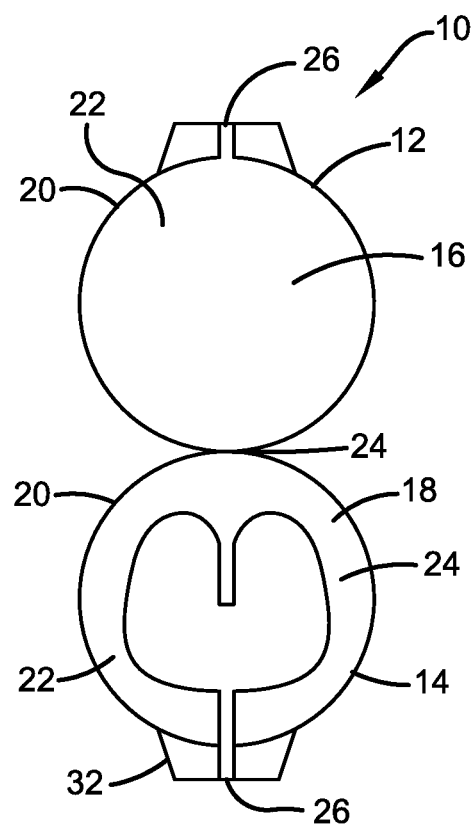
FIG. 1C is a top view of an exemplary protective case for an insulin infusion set in an open configuration.
Figure 2:
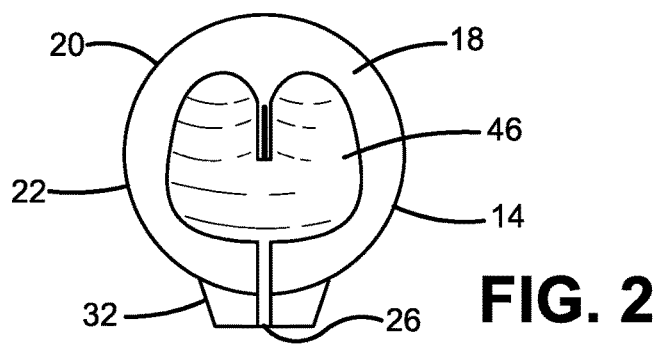
FIG. 2 is a top view of an interior portion of an exemplary protective case for an insulin infusion set.

According to further aspects of the present teaching, the bottom interior portion (18) of the first or second half shells (12) and (14) may include a mold (46) such as a hollowed out plastic cut-out, a foam mold, or a mold formed in any other type of material as shown in FIG. 2. The mold may have a cut-out in the shape of the needle, needle and hub or infusion set piece allowing for the needle, needle and hub, or insulin infusion set to be snapped or pushed into place. This prevents movement of the needle, needle and hub, or insulin infusion set in the interior portion of the protective container (10), thereby preventing accidental damage to the article by jostling of the article within the container as the protective container (10) is moved and/or transported. Thus, a secure means for storing and transporting the article is provided.

Figure 4A:
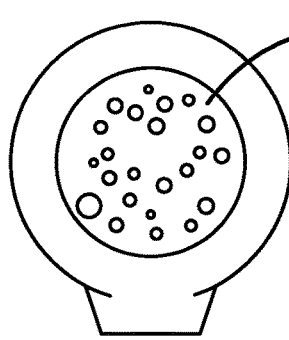
FIG. 4A is a top view of an exemplary insulin infusion set.
Figures 4B, 4C:
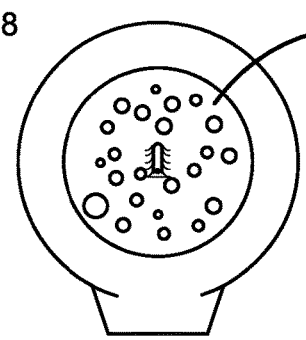
FIG. 4B is a top view of an interior portion of an exemplary protective case for an insulin infusion set showing a foam pad inserted therein.
FIG. 4C is a top view of an interior portion of an exemplary protective case for an insulin infusion set showing a foam pad having a raised portion inserted therein.

According to further aspects of the present teaching, the bottom interior portion (18) of the first or second half shells (12) and (14) may include a polyurethane or polyethylene foam (48) that the needle, needle and hub or infusion set (50) (as shown in FIG. 4A) may rest on inside of the protective case as shown in FIG. 4B. The foam may or may not include a mold or cut out for housing the needle, needle and hub or infusion set and may or may not be saturated with a sanitizer solution. In certain cases, the foam insert (48) may provide an additional advantage of providing a secure pressure fit and lock of the insulin infusion set in the interior of the protective case when case is in its closed configuration. In certain applications, it may be desirable to insert the needle of the insulin infusion set into the foam for additional protection and sanitization. Accordingly, in certain embodiments, the foam insert (48) may include a raised portion mirroring the shape of a needle into which the needle of an insulin infusion set may be inserted into. In other cases, the needle of an insulin infusion set may be positioned on the bottom side of the infusion set and point downward. In such cases, the foam insert (48) may provide a protective space into which the needle may be inserted therethrough. FIG. 20 illustrates a strip of foam inserts (48) having an adhesive backing which may be used to insert in the interior of the protective case (20). Similar strips having an adhesive backing may be used for sanitizer inserts or pads (38), protective container molds (46) for insertion inside the protective container (10) as well as for hook and loop connectors (58), snap connectors (62) and sleeves (54) for adhering to an insulin pump case.

As described above, the bottom interior portion (18) of the first or second half shells (12) and (14) may include a sanitizer insert or pad (38), a mold or cutout (46) or a polyurethane or polyethylene foam (48). It should be understood that in certain embodiments, one of the first or second half shells (12) and (14) may include any one of a sanitizer insert or pad, a mold or cutout or a polyurethane or polyethylene foam while the other of the first or second half shells may include any one of a sanitizer insert or pad, a mold or cutout or a polyurethane or polyethylene foam.

As further mentioned above, the first and second half shells (12) and (14) includes a top interior portion (16) and a rim portion (20). More specifically, the rim portion (20) is positioned at the top interior portion of the first and second half shells (12) and (14). According to certain aspects of the present teaching, the rim portion (20) and is present along the entire periphery of the top portion of the first and second half shells from a first side of the hinge (24) to a second side of the hinge (24). According to other aspects of the present teaching, the rim portion (20) and is present along a portion of the periphery of the top portion of the first and second half shells from a first side of the hinge (24) to a second side of the hinge (24). In certain embodiments, the rim portion (20) present on the first half shell (12) has a different circumferential size compared to the rim portion (20) present on the second half shell (14). This different circumferential size may allow for a snap fit or pressure fit connection when closing the first and second half shells (12) and (14) together. In other embodiments, the rim portion (20) may extend into or be present along a portion of or the entire the top portion of the port portion (32) allowing for a snap fit or pressure fit connection between the first and second half shells (12) and (14). The rim portion (20) located in the port portion (32) may be in addition to or in alternative to the rim portion present along the top portion of the main body of the protective container (10). In other embodiments, the protective container (10) may include a push button connector. The push button connector may include at least one latch (54) on one of the first or second half shells (12, 14) and at least one latch receiving portion (56) on one of the first or second half shells (12, 14) as shown for example in FIG. 8. The push button connector allows a user to press down on the first half shell (12) with respect to the second half shell (14) to release the latch and open the container and to press down on the first half shell (12) with respect to the second half shell (14) to latch and engage the first half shell (12) with the second half shell (14) to achieve a closed locked configuration.

The main body of the protective case (10) (i.e., the portion of the protective case (10) excluding the port portion (32)) may take the form of a variety of different shapes or configurations. For example, the main body of the protective case (10) may be circular in shape, triangular in shape, rectangular in shape, rectangular in shape or have any polygonal shape (see for example FIGS. 16 and 17, FIGS. 18A through 18D, FIGS. 19A through 19C and FIGS. 24A to 24C). According to certain aspects of the present teaching the first exterior portion (34) and a second exterior portion (36) of the first and second half shells (12) and (14) may be concave in shape, convex in shape, have an indented portion, have a flat or level planar shape, or have a thinned out or tapered side portion resulting in a corresponding shaped casing as shown in FIGS. 18A, 18B, 18C and 18D. The convex shaped protective case may provide additional spacing inside the protective case if desired, for example, to house a mold or sanitizing pad or to accommodate the convex shape of certain infusion sets. In other embodiments, a concave or indented shaped protective case may provide a means for securing the needle, needle and hub or insulin infusion set in place inside the protective case as it provides a pressure fit which inhibits movement within the interior of the protective case. A protective case having thinned out or tapered sides may provide a means for more easily inserting and removing the protective case inside a sleeve or inside a snap coupling positioned on the exterior of an insulin pump casing as described in greater detail below. Finally, protective cases having a flat or level shell case may provide extra space as needed for various types of inserts and insulin infusion sets and may accordingly represent a casing that may be used in various or multiple applications.

As explained above, according to certain aspects of the present teaching, it is desirable to attach the protective case (10) to a case used to house an insulin pump, i.e., an insulin pump case (40). This may be accomplished by one of several means. In a first means, this may be accomplished through use of a first hook and loop (e.g., Velcro) portion attached to either first exterior portion (34) or the second exterior portion (36) of either the first and second half shells (12) and

Figure 37A:
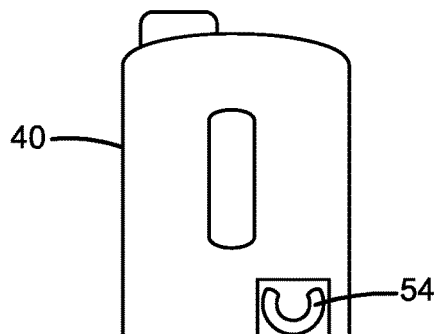
FIGS. 37A and 37B illustrate a front side view and a back side view of an insulin pump with a sleeve integrated or built into the front side of the insulin pump.
Figure 37B:
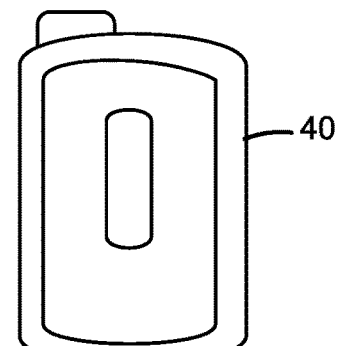
Figure 38A:
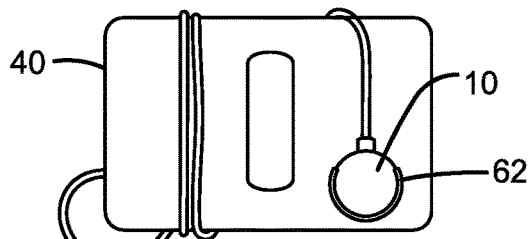
FIGS. 38A and 38B illustrate a front side view and a back side view of an insulin pump with a snap connector integrated or built into the front side of the insulin pump.
Figure 38B:
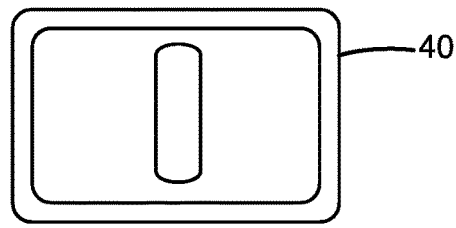
Figure 39A:
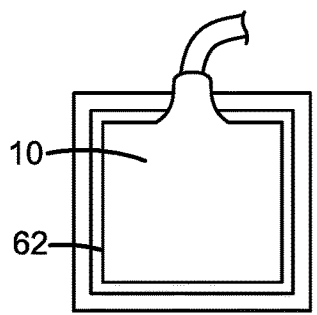
FIG. 39A illustrates an exemplary snap connector for a protective case for an insulin infusion set.
Figure 39B:
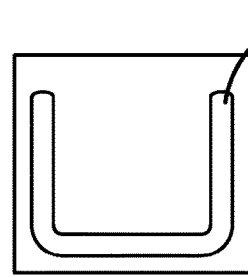
FIG. 39B illustrates an exemplary sleeve for a protective case for an insulin infusion set.
Figure 40A:
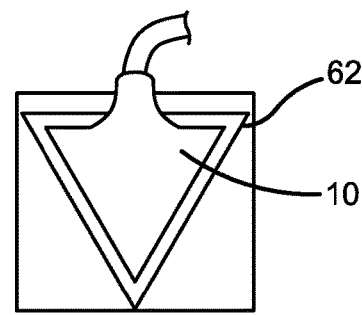
FIG. 40A illustrates an exemplary snap connector for a protective case for an insulin infusion set.
Figure 39C:
FIG. 39C is a side perspective view of an exemplary protective case for an insulin infusion set.
Figure 41:
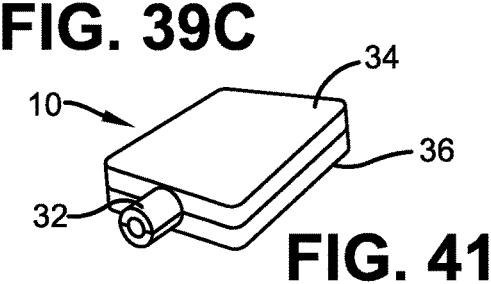
FIG. 41 illustrates an exemplary protective case for an insulin infusion set.
Figure 40B:
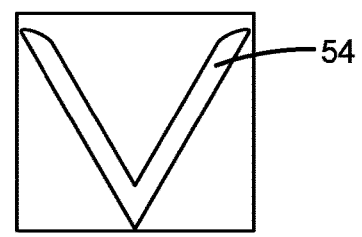
FIG. 40B illustrates an exemplary sleeve for a protective case for an insulin infusion set.

(14) and a second hook and loop (e.g., Velcro) portion attached to the housing of an insulin pump. Attachment of the first and second hook and loop portions may be achieved by pealing a backing (63) away from a backside of the hook and loop portion and exposing an adhesive (60) which may be engaged to the protective case (10) and the insulin pump housing (40). This is illustrated in FIGS. 21A and 21B. In a second means, the protective case (10) may engage an insulin pump case or insulin pump housing through a snap fit connection. This may be accomplished by one of several means. In a first embodiment, the insulin pump case or housing (40) may include a protective case snap connector (62) as shown in FIGS. 22A, 22B, 26A and 26B. The protective case snap connector (62) may be fitted onto the insulin pump case or housing (40) (e.g., by an adhesive, welding, plastic welding, or any other suitable means known to a person of ordinary skill in the art) or may be integrated into the insulin pump case or housing (40) in the manufacture of the insulin pump case or housing (40) (e.g., as a manufactured component of the insulin pump case). For example, the snap connector (62) may be formed from a mold integral within the insulin pump case or may constitute a cut-out in the insulin pump case. As shown in FIGS. 22A, 22B, 26A, 26B, 39A and 40A, the protective case snap connector (62) may have a shape that corresponds to the shape of the main body of the protective case (10) (e.g., it may have circular, square-like or rectangular, or triangular shape that is slightly larger than the shape of the protective case to allow for a snap fit connection around the periphery of the main body portion of the protective case). The protective case snap fit connector (62) may also include an opening to accommodate the port portion (32) which extends or protrudes out from the main body portion of the protective case. This opening in the protective case snap connector (62) allows the user or patient to manually use the port portion (32) as a lever to engage or disengage the protective case (10) to and from the protective case snap connector (42). An example of an insulin pump including a snap fit connector is illustrated in FIG. 46. In a second embodiment, the protective case (10) and the insulin pump case or housing (40) may include a button connector including a post end (68) and a recess or receiving end (66). The post end (68) of the button connector may be positioned on either the protective case (10) or the insulin pump case or housing (40) and the recess or receiving end (66) of the button connector may likewise, be positioned on either the protective case (10) or the insulin pump case or housing (40). An example of this embodiment is illustrated in FIG. 44. The components of the button connector may be either fitted onto the protective case (10) and insulin pump case or housing (40) or integrated into the protective case (10) and insulin pump case (40) during manufacture. According to a further aspect of the present teaching, the insulin pump case or housing (40) may include a sleeve (54) for housing the protective case (10). The sleeve (54) may be of a shape corresponding to the shape of the protective case (10). For example, the sleeve may be triangular, square-like in shape or circular as shown in FIGS. 25A, 25B, 39B, and 40B. Moreover, the sleeve (54) may be attached to the insulin pump case or housing (40) with an adhesive (60) exposed by peeling away a backing (63) or may integrated into the insulin pump or casing (40) during manufacture (e.g., as a manufactured component of the insulin pump or casing). The sleeve (54) may be made from any material (e.g., a plastic or metal) as deemed suitable by a person of ordinary skill in the art. Examples of the sleeve (54) on an insulin pump are illustrated in FIG. 37A and FIG. 45.

Also provided is a method of making a protective case for an insulin infusion set which includes the steps of providing a first half shell having a front side, a back side a top interior portion, a rim portion and a first exterior portion; providing a second half shell having a front side, a back side, a bottom interior portion, a rim portion and a second exterior portion; connecting the first half shell to the second half shell by providing a hinge which connects the back side of the first half shell to the back side of the second half shell, wherein the hinge allows the first half shell and second half shell to rotate with respect to each other between an open configuration and a closed configuration; forming an interior portion with the first half shell and second half shell of the protective case; forming a port in the protective case, wherein the port is formed from a port passageway formed at the front side of the first half shell and the front side of the second half shell when the first half shell and the second half shell are in a closed configuration. The protective case may include any number of additional steps necessary for incorporating, forming, connecting, attaching any number of additional features of the protective case set forth herein.

Also provided is a method of making an insulin pump case. The method includes the following steps: providing an insulin pump comprising a housing; providing an insulin pump attachment mechanism which is used to engage the protective case to the housing of the insulin pump, wherein the insulin pump attachment mechanism comprises a hook and loop fastener; attaching a first fastener comprising a hook or loop to either the first exterior portion of the first half shell or the second exterior portion of the second half shell of the protective case; providing a corresponding second fastener, comprising a hook if the first fastener is a loop or loop if the first fastener is a hook and attaching the second fastener to the housing of the insulin pump. In an alternative method, the insulin pump attachment mechanism comprises a protective case snap connector. In this method, the snap connector is fitted onto the housing of an insulin pump for connecting the protective case to the housing of the insulin pump through an adhesive backing. Alternatively, the method may comprise the step of molding or forming a snap connector or snap connector shape into the body of the insulin pump case. In an alternative method, the insulin pump attachment mechanism comprises a button connector comprising a post end and a receiving end wherein one of the post end and the receiving end is positioned on one of the first exterior surface of the first half shell or the second exterior surface of the second half shell and wherein the opposing post end or receiving end is positioned on the housing of the insulin pump. In this method, the post member may be formed, molded or shaped onto the first exterior surface of the first half shell, the second exterior surface of the second half shell or the insulin pump case and the receiving end may be formed, molded or shaped onto either the first exterior surface of the first half shell or the second exterior surface of the second half shell or the insulin pump case depending on the location of the post member. In an alternative method, the insulin pump attachment mechanism comprises the step of attaching, adhering, forming, molding or shaping a sleeve onto the housing of the insulin pump for receiving the protective case, wherein the sleeve is formed into a shape which corresponds to the shape of the protective case. The insulin pump case and protective case may include any number of additional steps necessary for incorporating, forming, molding, shaping, connecting, attaching, adhering any number of additional features of the protective case set forth herein.

While the protective case for an insulin infusion set has been described with reference to various exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential cope thereof. Therefore, it is intended that the invention not be limited to the particular embodiment disclosed as the bet mode contemplated for carrying out the invention, but that the invention will include all embodiments falling within the scope of the appended claims. Further, the "invention" as that term is used in this document is what is claimed in the claims of this document. The right to claim elements and/or sub-combinations that are disclosed herein as other inventions in other patent documents is hereby unconditionally reserved.

Having thus described the disclosed method and apparatus, it is now claimed:

1. A protective case for an insulin infusion set comprising:
    a first half shell having a front side, a back side a top interior portion, a rim portion and a first exterior portion;
    a second half shell having a front side, a back side, a bottom interior portion, a rim portion and a second exterior portion;
    a hinge connecting the back side of the first half shell to the back side of the second half shell, wherein the hinge allows the first half shell and second half shell to rotate with respect to each other between an open configuration and a closed configuration;
    an interior portion formed by the first half shell and second half shell of the protective case;
    a port, wherein the port is formed from a port passageway formed at the front side of the first half shell and the front side of the second half shell when the first half shell and the second half shell are in a closed configuration,
    wherein the top interior portion of the first half shell and the bottom interior portion of the second half shell each includes one of a sanitizer insert or pad, a mold cutout in the shape a needle or a needle and hub of an insulin infusion set or a polyurethane or polyethylene foam pad; wherein the sanitizer insert or pad, mold cutout, or polyurethane or polyethylene foam pad may optionally be saturated in a sanitizer solution; or
    wherein one of the top interior portion of the first half shell or the bottom interior portion of the second half shell includes one of a sanitizer insert or pad, a mold cutout in the shape a needle or a needle and hub of an insulin infusion set or a polyurethane or polyethylene foam pad, wherein the sanitizer insert or pad, mold cutout, or polyurethane or polyethylene foam pad may optionally be saturated in a sanitizer solution and the other of the top interior portion of the first half shell or the bottom interior portion of the second half shell is empty.

2. The protective case for an insulin infusion set of claim 1, wherein the port passageway at the front side of the first half shell and the port passageway at the front side of the second half shell is hemi-circular, hemi-cylindrical, hemi-spherical, hemi-prismal, or hemi-conical in shape and extends toward the interior portion of the protective case when the protective case is in the open configuration and wherein the port passageway at the front side of the first half shell and the front side of the second half shell is circular, cylindrical, spherical, prismal or conical in shape and extends toward the interior portion of the protective case when the protective case is in the closed configuration.

3. The protective case for an insulin infusion set of claim 2, wherein the port passageway is formed from a hemi-circular or hemi-cylindrical indentation along the rim of the first half shell and the rim of the second half shell.

4. The protective case for an insulin infusion set of claim 2, wherein the port passageway on the first half shell and the port passageway on the second half shell when in the closed configuration forms one of a conical shaped port, a spherical shaped port, a triangular shaped port, a square or cubical shaped port, a rectangular shaped port, a pentagonal shaped port, a hexagonal shaped port, a heptagonal shaped port, an octagonal shaped port, a nonagonal shaped port, a decagonal shaped port, or a star shaped port having from 5 to 10 points.

5. The protective case for an insulin infusion set of claim 2, wherein the port passageway includes a seal along a periphery of its opening, wherein the seal is formed by a seal portion positioned along a periphery of the port passageway of the first half shell and along a periphery of the port passageway of the second half shell.

6. The protective case for an insulin infusion set of claim 2, wherein the port passageway of the protective case is formed in a port portion of the protective case, wherein the port portion is formed from an outward symmetrical protection of a primary shape of the first half shell and the second half shell of the protective case, wherein the port portion includes the port passageway, when the first half shell and the second half shell are in the closed configuration.

7. The protective case for an insulin infusion set of claim 1, the bottom interior portion includes a sanitizer positioned therein, wherein the sanitizer is in the form of a fluid or a sanitizer pad, wherein the sanitizer pad is an alcohol pad.

8. The protective case for an insulin infusion set of claim 1, wherein the top interior portion of the first half shell and/or the bottom interior portion of the second half shell includes a mold having a cut-out in the shape of a needle or a needle and hub of an insulin infusion set.

9. The protective case for an insulin infusion set of claim 1, wherein the top interior portion of the first half shell and/or the bottom interior portion of the second half shell includes a polyurethane or polyethylene foam that a needle or a needle and hub of an insulin infusion set may rest upon.

10. The protective case of an insulin infusion set of claim 1, wherein the rim portion of the first half shell extends at least a portion along the periphery of the top interior portion from a first side of the hinge to a second side of the hinge and wherein the rim portion of the second half shell extends at least a portion along the periphery of the bottom interior portion from the first side of the hinge to the second side of the hinge, wherein the rim portion of the first half shell has a different circumferential size than the rim portion of the second half shell allowing for a snap fit or pressure fit connection when the first half shell and the second half shell are in the closed configuration.

11. The protective case of an insulin infusion set of claim 1, wherein the first half shell and the second half shell, excluding the port form a main body of the protective case, wherein the main body of the protective case may have a circular or polygonal shape.

12. The protective case of an insulin infusion set of claim 1, wherein the first exterior portion of the first half shell and/or the second exterior portion of the second half shell is concave in shape, convex in shape, has an indented portion, has a flat or level planar shape or has a tapered side portion around its circumference.

13. The protective case of an insulin infusion set of claim 1, wherein the protective case is made from a plastic material, a synthetic fabric, a natural fabric or a metal.

14. The protective case of an insulin infusion set of claim 13, further wherein the protective case comprises a hardened material or a pliable material.

15. The protective case of an insulin infusion set of claim 1, wherein the port comprises a first side portion and a second side portion, wherein the first side portion and second side portion of the port comprises an angled cut-out portion in the closed configuration, wherein the angled cut-out portion is formed from a port portion of the first half shell having an angled portion on the first side portion and second side portion of the first half shell port portion and a port portion of the second half shell having an angled portion of the first side portion and the second side portion of the second half shell port portion.

16. The protective case of an insulin infusion set of claim 1, wherein the protective case comprises a push button latching mechanism positioned on the front side of the protective case.

17. A kit comprising:
an insulin infusion set comprising a needle, a hub and a cannula; and
a protective case for storing the needle and the hub of an insulin infusion set, wherein the protective case comprises:
a first half shell having a front side, a back side, a top interior portion, a rim portion and a first exterior portion;
a second half shell having a front side, a back side, a bottom interior portion, a rim portion and a second exterior portion;
a hinge connecting the back side of the first half shell to the back side of the second half shell, wherein the hinge allows the first half shell and second half shell to rotate with respect to each other between an open configuration and a closed configuration;
an interior portion formed by the first half shell and second half shell of the protective case;
a port, wherein the port is formed from a port passageway formed at the front side of the first half shell and the front side of the second half shell when the first half shell and the second half shell are in a closed configuration,
wherein the top interior portion of the first half shell and the bottom interior portion of the second half shell each includes one of a sanitizer insert or pad, a mold cutout in the shape a needle or a needle and hub of an insulin infusion set or a polyurethane or polyethylene foam pad; wherein the sanitizer insert or pad, mold cutout, or polyurethane or polyethylene foam pad may optionally be saturated in a sanitizer solution; or
wherein one of the top interior portion of the first half shell or the bottom interior portion of the second half shell includes one of a sanitizer insert or pad, a mold cutout in the shape a needle or a needle and hub of an insulin infusion set or a polyurethane or polyethylene foam pad, wherein the sanitizer insert or pad, mold cutout, or polyurethane or polyethylene foam pad may optionally be saturated in a sanitizer solution and the other of the top interior portion of the first half shell or the bottom interior portion of the second half shell is empty.

18. A kit comprising:
an insulin infusion set comprising a needle, a hub and a cannula;
a protective case for storing the needle and the hub of an insulin infusion set, wherein the protective case comprises:
a first half shell having a front side, a back side a top interior portion, a rim portion and a first exterior portion;
a second half shell having a front side, a back side, a bottom interior portion, a rim portion and a second exterior portion;
a hinge connecting the back side of the first half shell to the back side of the second half shell, wherein the hinge allows the first half shell and second half shell to rotate with respect to each other between an open configuration and a closed configuration;
an interior portion formed by the first half shell and second half shell of the protective case;
a port, wherein the port is formed from a port passageway formed at the front side of the first half shell and the front side of the second half shell when the first half shell and the second half shell are in a closed configuration;
an insulin pump comprising a housing, and
an insulin pump attachment mechanism which is used to engage the protective case to the housing of the insulin pump, wherein the insulin pump attachment mechanism comprises one of the following: i) a hook and loop fastener, wherein a first fastener comprising a hook or loop is attached to either the first exterior portion of the first half shell or the second exterior portion of the second half shell and a corresponding second fastener, comprising a hook if the first fastener is a loop or loop if the first fastener is a hook, is attached to the housing of the insulin pump, ii) a protective case snap connector fitted onto the housing of an insulin pump for connecting the protective case to the housing of the insulin pump, iii) a button connector comprising a post end and a receiving end wherein one of the post end and the receiving end is positioned on one of the first exterior surface of the first half shell or the second exterior surface of the second half shell and wherein the opposing post end or receiving end is positioned on the housing of the insulin pump and iv) a sleeve positioned on the housing of the insulin pump for receiving the protective case, wherein the sleeve has a shape which corresponds to the shape of the protective case.

19. A protective case for an insulin infusion set comprising:
a first half shell having a front side, a back side a top interior portion, a rim portion and a first exterior portion;
a second half shell having a front side, a back side, a bottom interior portion, a rim portion and a second exterior portion;
a hinge connecting the back side of the first half shell to the back side of the second half shell, wherein the hinge allows the first half shell and second half shell to rotate with respect to each other between an open configuration and a closed configuration;
an interior portion formed by the first half shell and second half shell of the protective case;
a port, wherein the port is formed from a port passageway formed at the front side of the first half shell and the front side of the second half shell when the first half shell and the second half shell are in a closed configuration; and, an insulin pump attachment mechanism, wherein the insulin pump attachment mechanism comprises one of the following: i) a hook and loop fastener, wherein a first fastener comprising a hook or loop is attached to either the first exterior portion of the first half shell or the second exterior portion of the second half shell and a corresponding second fastener, comprising a hook if the first fastener is a loop or a loop if the first fastener is a hook, is attached to a housing of an insulin pump, ii) a protective case snap connector fitted onto the housing of an insulin pump for connecting the protective case to the housing of the insulin pump, iii) a button connector comprising a post end and a receiving end wherein one of the post end and the receiving end is positioned on one of the first exterior surface of the first half shell or the second exterior surface of the second half shell and wherein the opposing post end or receiving end is positioned on the housing of the insulin pump and iv) a sleeve positioned on the housing of the insulin pump for receiving the protective case, wherein the sleeve has a shape which corresponds to the shape of the protective case.

* * * * *